United States Patent
Yao et al.

(10) Patent No.: US 8,802,824 B2
(45) Date of Patent: Aug. 12, 2014

(54) MODIFIED RECOMBINANT HUMAN ENDOSTATIN AND USES THEREOF

(75) Inventors: Wenbing Yao, Jiangsu (CN); Hong Tian, Jiangsu (CN); Xiangyang Xu, Jiangsu (CN); Hairui Li, Jiangsu (CN); Yue Dong, Jiangsu (CN); Xiangdong Gao, Jiangsu (CN)

(73) Assignees: Jiangsu Simcere Pharmaceutical R&D Co., Ltd., Jiangsu (CN); Shandong Xiansheng Maidejin Biological Pharmaceutical Co., Ltd., Shandong (CN)

( * ) Notice: Subject to any disclaimer, the term of this patent is extended or adjusted under 35 U.S.C. 154(b) by 962 days.

(21) Appl. No.: 12/676,766

(22) PCT Filed: Sep. 4, 2008

(86) PCT No.: PCT/CN2008/072261
§ 371 (c)(1),
(2), (4) Date: Mar. 5, 2010

(87) PCT Pub. No.: WO2009/033406
PCT Pub. Date: Mar. 19, 2009

(65) Prior Publication Data
US 2010/0210822 A1    Aug. 19, 2010

(30) Foreign Application Priority Data
Sep. 5, 2007   (CN) .......................... 2007 1 0131562

(51) Int. Cl.
*A61K 38/17* (2006.01)
*C07K 14/78* (2006.01)
*A61K 47/48* (2006.01)
*A61K 38/00* (2006.01)

(52) U.S. Cl.
CPC ........... *C07K 14/78* (2013.01); *A61K 47/48215* (2013.01); *A61K 38/00* (2013.01)
USPC .......................................... 530/356; 530/402

(58) Field of Classification Search
None
See application file for complete search history.

(56) References Cited

U.S. PATENT DOCUMENTS

2010/0285103 A1* 11/2010 Luo et al. ...................... 424/450

FOREIGN PATENT DOCUMENTS

CN          1891717 A    *  1/2007
WO    WO 2007/082483    *  7/2007 ............. A61K 38/17

OTHER PUBLICATIONS

Roberts et al., "Chemistry for peptide and protein PEGylation", Advanced Drug Delivery Reviews 54 (2002) 459-476.*
English Machine Translation of CN 1891717, Jan. 10, 2007.*

* cited by examiner

*Primary Examiner* — Suzanne M Noakes
(74) *Attorney, Agent, or Firm* — WPAT, P.C.; Anthony King

(57) ABSTRACT

Provided is a kind of modified recombinant human endostatin that has the structure of $CH_3O-(CH_2CH_2O)_m-CH_2CH_2CH_2-N^{\alpha}H$-Endostar, wherein the average molecular weight of $CH_3O-(CH_2CH_2O)_m-CH_2CH_2CH_2-$ is 20-40 kD. The modified recombinant human endostatin enhances the stability in vivo, improves blood drug concentration, prolongs half-life, markedly increases the activity of inhibiting the endothelial cells proliferation, thus reduces drug dosage and decreases administration frequency. Its application for preparing anti-tumor pharmaceutical compositions is also provided.

1 Claim, 5 Drawing Sheets

1 2 3 4

1 2 3 4

MODIFIED RECOMBINANT HUMAN ENDOSTATIN AND USES THEREOF

BACKGROUND OF THE INVENTION

1. Field of Invention

The present invention relates to the field of biopharmacy, and in particular to a modified recombinant human endostatin and application thereof.

2. Related Art

With the viewpoint of "tumor growth dependence on neoangiogenesis" proposed by Professor Folkman in 1971, it is possible to control tumor growth by blocking neoangiogenesis, to achieve the object of inhibiting tumor invasion, recurrence and metastasis, thus creating a new field in tumor therapy.

In 1997, it was found by O'Reilly, et al. in Harvard University that, the culture medium of mouse hemangioendothelioma endothelial cells had inhibitory effect on endotheliocytes, and by purification, such active species exhibited dose-dependent growth inhibition endotheliocytes specifically in a certain concentration range (100 ng/ml-600 ng/ml). It is indicated by N-terminal amino acid sequencing that, such species is C-terminal fragment of collagen XVIII, with a molecular weight of about 20 kD, and such protein is named as endostatin (ES).

Studies show that the endostatin can effectively control growth, infiltration and metastases of various solid tumors, such as non-small cell lung cancer, colon cancer, brain glioma, fibroma, mesothelioma and lymphomata. Presently, endostatin is obtained through genetic engineering method. Due to too high cost of expression of endostatin by fungi, it is a trend towards utilisation of E. coli as the expression system, but the expressed protein has the problem of low renaturation and the like. To this end, the attempts to modify the structure of natural endostatin are initiated. 9 amino acids are added at the N-terminal of the natural endostatin by Luo Yongzhang, et al., and as a result, ES stability is enhanced, and half life is prolonged, bioactivity is improved, and the renaturation of the protein is higher than that of general production method. This medicament has been put into market, under the trade name of Endostar. The produced recombinant human endostatin consists of 192 amino acids, and the amino acid sequence is:

```
(M) GGSHHHHHHSHRDFQPVLHLVALNSPLSGGMRGIRGADFQCFQQARA

VGLAGTFRAFLSSRLQDLYSIVRRADRAAVPIVNLKDELLFPSWEALFSG

SEGPLKPGARIFSFDGKDVLRHPTWPQKSVWHGSDPNGRRLTESYCETWR

TEAPSATGQASSLLGGRLLGQSAASCHHAYIVLCIENSFMTASK,
in which, when being expressed by E. coli, Met at
the N-terminal may be deleted in some cases
(SEQ ID NO. 1 or SEQ ID NO. 2).
```

The clinical experiments at phase III indicates that, the modified endostatin may have a certain synergetic effect when being used in combination with chemotherapeutant NP, and be capable of prolonging the tumor progression in patients.

It is confirmed by clinical experiments that the endostatin has little adverse effects and is suitable for use in combination with radiotherapy or chemotherapy. However, as the small molecule protein, the endostatin is unstable in properties, and it is indicated by studies that endostatin is likely degraded under anoxic condition (after the endostatin is co-incubated with endotheliocytes in hypoxia environment for 48 hours, the content will be decreased by about 20%). The environment inside the tumor is a hypoxia environment, thus being particularly favorable for exerting its activity. On the other hand, currently, the clinical dosage of Endostar is as high as 7.5 mg/m$^2$, and is administrated by intravenous drip for 3-4 hours daily. Experiments show that, when being administrated by intraperitoneal injection, the endostatin is cleared in 2 hours. These indicate that, after being introduced into body, the endostatin may be hydrolyzed by the proteolytic enzyme, particularly at tumor site where the drug plays a pharmacodynamics. It is a problem to be solved urgently how to protect the protein molecule against enzymolysis and reduce clearance, thereby reducing the dosage.

Polyethylene glycol (PEG) is a safety, non-active and non-toxic polymer. By covalent attachment to the protein for chemical modification, the pegylation is able to effectively overcome the disadvantages of protein type drugs in the clinical application, for example prolong the half life of plasma, increase bioavailability, reduced protein immunogenicity, improve curative effect of drugs and safety and so on, while maintaining the biological activity of natural protein. Till now, the PEG-modified protein polypeptide drugs that have been successfully marketed include adenosine deaminase (Adagen®), asparaginase (OncasPar®), interferon α-2b (PEG-intron®), interferon α-2a (Pegasys®) etc., also more than 20 drugs, such as, uricase, hirudin, interleukin-2, interleukin-6 are under clinical studies.

During the pegylation of protein, activated PEG molecules are coupled to the free amino groups, mainly Lys, of the protein molecule. Because there is not only one free amino group in the protein chain, there are several types of modified products in the reaction products, such as, monomolecular, bimolecular, and even trimolecular products. Further, the modified products also include many types of isomers. Compared with monomolecular modified products, the loss of activity of the multimolecular modified products is higher, thus not only leading to the waste of reaction substrates, but also the reduction of overall activity of the reaction products. The problem of multimolecular modified products can be solved by controlling the reaction conditions and adopting purification means, to obtain monomolecular modified products. However, the problem of isomers in monomolecular modification still exists. Further, there may be great difference in the bioactivity of the isomers, and the mixture of the isomers is generally difficult to be purified. Therefore, it is desirable to achieve site-directed modification by controlling the reaction conditions, to promote purification and property studies of the products. Furthermore, the site-directed modification is more favorable for keeping protein activity. A method invented by Kinstler is to take advantage of lower pKa value of α-amino at the N-terminal than amino of lysine. Pegfilgrastim® is obtained by modifying granulocyte colony stimulating factor (G-CSF) with PEG acetaldehyde.

SUMMARY OF THE INVENTION

The present invention is directed to a modified recombinant human endostatin $CH_3O-(CH_2CH_2O)_m-CH_2CH_2CH_2-N^\alpha H$-Endostar, which enhances the stability of Endostar in vivo, increases effective blood drug concentration, prolongs the half life and reduces the drug dosage. The weight average molecular weight of $CH_3O-(CH_2CH_2O)_m-CH_2CH_2CH_2-$ is 20 kD-40 kD, a preferred weight average molecular weight of $CH_3O-(CH_2CH_2O)_m-CH_2CH_2CH_2-$ is 20 kD (expressed by m=20 kD), another preferred weight average molecular weight of $CH_3O$—$(CH_2CH_2O)_m$—$CH_2CH_2CH_2$— is 40 kD (expressed by m=40 kD), with a dispersity ≤1.2 and a preferred dispersity of 1.1.

The present invention is further directed to an application of the modified recombinant human endostatin $CH_3O$—$(CH_2CH_2O)_m$—$CH_2CH_2CH_2$—$N^\alpha H$-Endostar in the preparation of anti-tumor drugs.

The objectives of the present invention are achieved by the following measure.

1. N-terminal chemical modification of Endostar. The reaction formula is as follows:

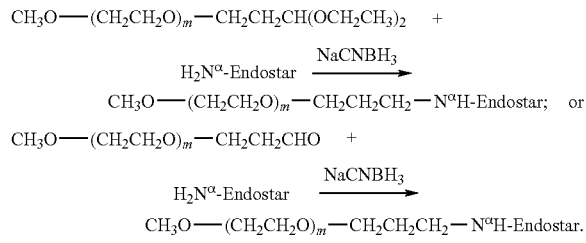

(1) Source of Endostar: The recombinant human vascular endostatin useful in the present invention is from Jiangsu Simcere-Medgenn Bio-pharmaceutical Co., Ltd. It is the endostatin with additional amino acid sequence (Met)GlyGlyXaaHisHisHisHisHis at the N-terminal expressed by E. coli, and has a molecular weight of 21 kD, in which Xaa represents the neutral amino acid or is absent, and when being expressed by E. coli, Met at the N-terminal may be deleted in some cases.

(2) The recombinant human vascular endostatin useful in the present invention reacts with monomethyl polyethylene glycol derivatives in the presence of the reducing agent sodium cyanoborohydride (final concentration of 10 mM-30 mM) at 0° C.-25° C. for 10 h-40 h, to give $CH_3O$—$(CH_2CH_2O)_m$—$CH_2CH_2CH_2$—$N^\alpha H$-Endostar.

The present invention has the following beneficial effects.

The modified recombinant human endostatin ($CH_3O$—$(CH_2CH_2O)_m$—$CH_2CH_2CH_2$—$N^\alpha H$-Endostar) of the present invention has the following advantages:

(1) The in vivo effective blood drug concentration of $CH_3O$—$(CH_2CH_2O)_m$—$CH_2CH_2CH_2$—$N^\alpha H$-Endostar is higher compared with that of Endostar;

(2) The activity of inhibiting endotheliocyte proliferation of $CH_3O$—$(CH_2CH_2O)_m$—$CH_2CH_2CH_2$—$N^\alpha H$-Endostar is increased significantly compared with that of Endostar;

(3) The in vivo half life of $CH_3O$—$(CH_2CH_2O)_m$—$CH_2CH_2CH_2$—$N^\alpha H$-Endostar is longer compared with that of Endostar;

(4) The AUC of $CH_3O$—$(CH_2CH_2O)_m$—$CH_2CH_2CH_2$—$N^\alpha H$-Endostar is higher compared with that of Endostar.

The advantages show that, for the modified Endostar, the in vivo stability is enhanced, the blood drug concentration is increased, the half life prolonged, and the activity of inhibiting endotheliocyte proliferation is significantly increased, thus reducing the drug dosage, decreasing the administration frequency, alleviating the physical affliction of patient and relieving the economical burden of patient. The $CH_3O$—$(CH_2CH_2O)_m$—$CH_2CH_2CH_2$—$N^\alpha H$-Endostar is useful in the preparation of anti-tumor drugs.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Hereinafter, the present invention is further described with reference to the embodiments below, which are not intended to limit the protection scope of the present invention.

Embodiment 1 Preparation of a Coupling Compound of $CH_3O$—$(CH_2CH_2O)_{20\ kD}$—$CH_2CH_2CH(OCH_2CH_3)_2$ with a Weight Average Molecular Weight of 20 kd with Endostar (Abbreviated as $PEG_{20}$-ENDO)

Figure 1:
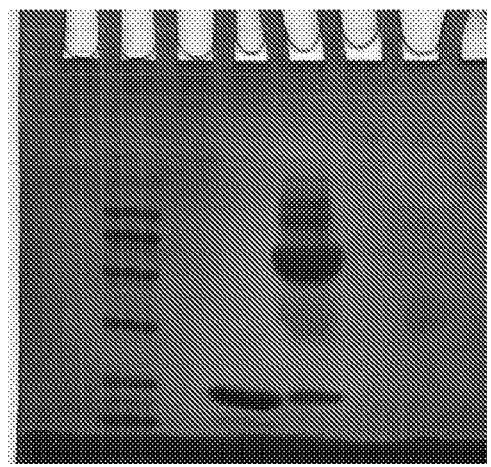
FIG. 1 shows the coupling of $CH_3O$—$(CH_2CH_2O)_{20\ kD}$—$CH_2CH_2CH(OCH_2CH_3)_2$ with Endostar, in which electrophoresis lanes 1-4 in respectively correspond to: 1. the standard proteins with molecular weights of 14400, 20100, 31000, 43000, 66200, 97400 respectively; 2. Endostar; 3. the reactant mixture; 4. $CH_3O$—$(CH_2CH_2O)_{20\ kD}$—$CH_2CH_2CH(OCH_2CH_3)_2$.

(1) Coupling of $CH_3O$—$(CH_2CH_2O)_{20\ kD}$—$CH_2CH_2CH(OCH_2CH_3)_2$ with Endostar To 20 ml Endostar stock solution (PH 5.0-5.5, HAC/NaAC Buffer, protein content of 5 mg/ml), the reducing agent sodium cyano-borohydride $NaCNBH_3$ was added to a final concentration of 20 mM, and 100 mg monomethoxy polyethylene glycol-3,3-diethoxy propane was added to a molar ratio of monomethoxy polyethylene glycol-3,3-diethoxy propane to Endostar of 1:1, and stirred over night at 4° C., to form the $PEG_{20}$-ENDO modification products, which were identified by SDS-PAGE. The identification results are as shown in FIG. 1.

(2) Purification of $PEG_{20}$-ENDO

Figure 2:
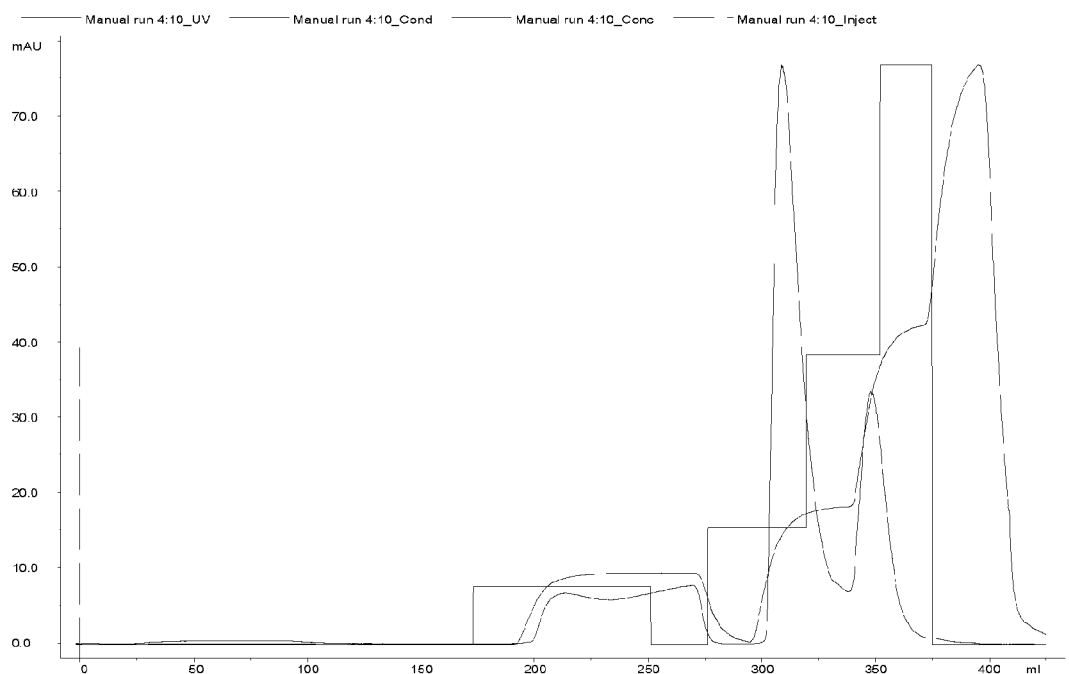
FIG. 2 is a chromatography diagram of purification of $CH_3O$—$(CH_2CH_2O)_{20\ kD}$—$CH_2CH_2CH_2$—$N^\alpha H$-Endostar.
Figure 3:
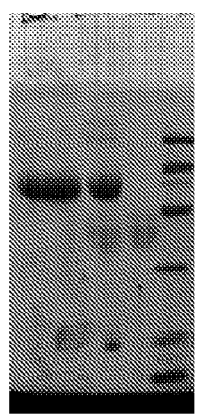
FIG. 3 shows a SDS-PAGE identification of $CH_3O$—$(CH_2CH_2O)_{20\ kD}$—$CH_2CH_2CH_2$—$N^\alpha H$-Endostar after purification, in which electrophoresis lanes 1-4 respectively correspond to: 1. $CH_3O$—$(CH_2CH_2O)_{20\ kD}$—$CH_2CH_2CH_2$—$N^\alpha H$-Endostar after purification; 2. the reaction mixture; 3. $CH_3O$—$(CH_2CH_2O)_{20\ kD}$—$CH_2CH_2CH(OCH_2CH_3)_2$; 4. the standard proteins with molecular weight of 14400, 20100, 31000, 43000, 66200, 97400 respectively.

The reaction products were separated and purified by CM-Sepharose column and AKTA chromatography. The samples were injected after being diluted with 20 mM, pH 7.0 PB buffer, equilibrated with 20 mM, pH 7.0 PB buffer to baseline, then eluted stepwisely with 20 mM, pH 7.0 PB buffers containing 0.1 M, 0.2 M, 0.5 M NaCl respectively (FIG. 2), and collected by a fraction collector. The modified products were identified by SDS-PAGE. (FIG. 3)

Embodiment 2 Preparation of a Coupling Compound of $CH_3O$—$(CH_2CH_2O)_{40\ kD}$—$CH_2CH_2CHO$ with a Weight Average Molecular Weight of 40 kd with Endostar (Abbreviated as $PEG_{40}$-ENDO)

(1) Coupling of $CH_3O$—$(CH_2CH_2O)_{40\ kD}$—$CH_2CH_2CHO$ with Endostar

Figure 4:
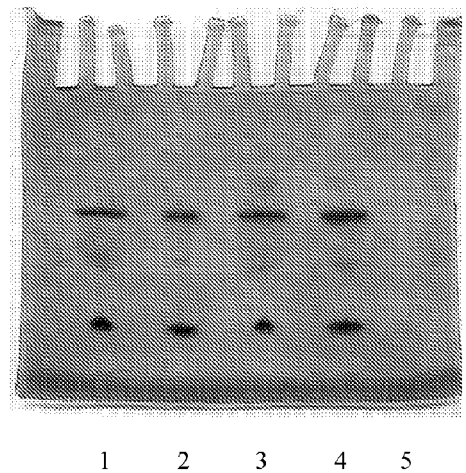
FIG. 4 shows the coupling of $CH_3O$—$(CH_2CH_2O)_{40\ kD}$—$CH_2CH_2CHO$ with Endostar, in which the electrophoresis lanes 1-5 respectively correspond to: 1-4. the reaction mixtures; 5. $CH_3O$—$(CH_2CH_2O)_{40\ kD}$—$CH_2CH_2CHO$.

To 20 ml Endostar stock solution (PH 5.0-5.5, HAC/NaAC Buffer, protein content of 5 mg/ml), the reducing agent sodium cyano-borohydride $NaCNBH_3$ was added to a final concentration of 20 mM, and 400 mg monomethoxy polyethylene glycol-3,3-diethoxy propane was added to a molar ratio of monomethoxy polyethylene glycol-3,3-diethoxy propane to Endostar of 1:2r, and stirred over night at 4° C., to form the $PEG_{40}$-ENDO modification products, which were identified by SDS-PAGE. (FIG. 4)

(2) Purification of $PEG_{40}$-ENDO

Figure 5:
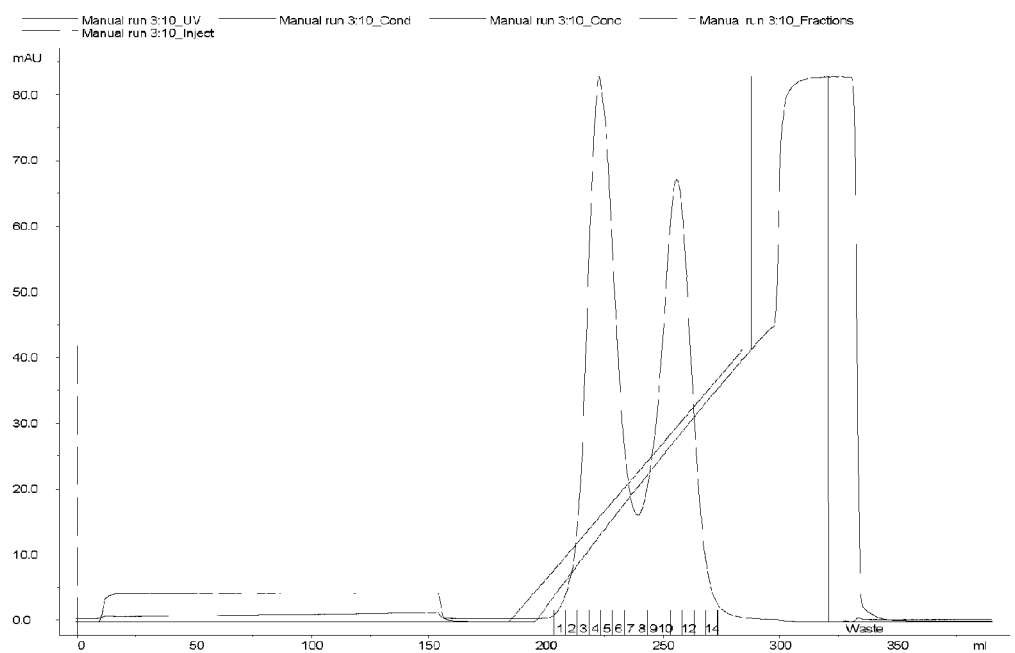
FIG. 5 is a chromatography diagram of purification of $CH_3O$—$(CH_2CH_2O)_{40\ kD}$—$CH_2CH_2CH_2$—$N^\alpha H$-Endostar.
Figure 6:
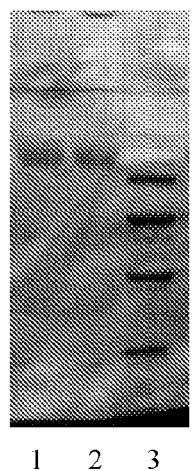
FIG. 6 shows a SDS-PAGE identification of $CH_3O$—$(CH_2CH_2O)_{40\ kD}$—$CH_2CH_2CH_2$—$N^\alpha H$-Endostar after purification, in which electrophoresis lanes 1-3 respectively correspond to: 1-2. $CH_3O$—$(CH_2CH_2O)_{40\ kD}$—$CH_2CH_2CH_2$—$N^\alpha H$-Endostar after purification; 3. the standard proteins with molecular weights of 14400, 20100, 31000, 43000, 66200, 97400 respectively.

The reaction products were separated and purified by CM-Sepharose column and AKTA chromatography. The sample were injected after being diluted with 20 mM, pH 7.0 PB buffer, equilibrated with 20 mM, pH 7.0 PB buffer to baseline, then eluted gradiently with 20 mM, pH 7.0 PB buffers containing 0-0.5 M NaCl respectively (FIG. 5), and collected in a fraction collector. The modified products were identified by SDS-PAGE. (FIG. 6)

Figure 7:
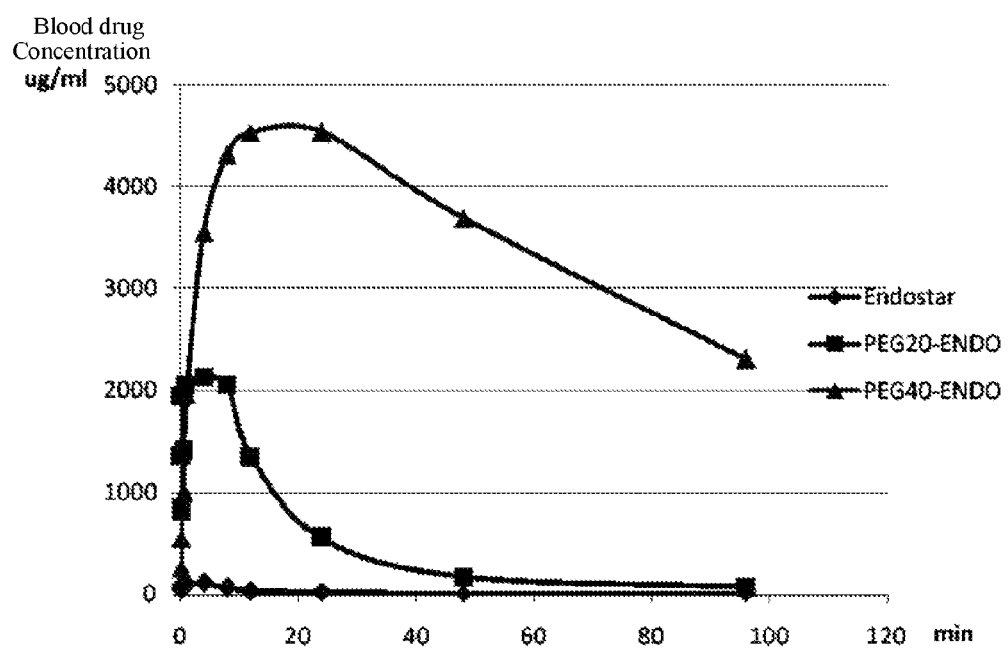
FIG. 7 is a relationship curve of blood drug concentrations of Endostar before and after modification over time.

Embodiment 3 Pharmacokinetics Study of Polyethylene Glycol-Modified Recombinant Human Endostatin 15 male SD rats were divided into 3 groups randomly and dosed with 45 mg/kg weight. Group A was dosed with unmodified Endostar, group B with $PEG_{20}$-ENDO, and group C with $PEG_{40}$-ENDO. Blood samples were taken at 5 min, 10 min, 15 min, 30 min, 1 h, 4 h, 6 h, 12 h, 24 h, 48 h, 96 h after dosing with haparin anticoagulant and centrifuged immediately at 6000 r/min for 10 min, to give the plasma samples. The content of the samples in the plasma were measured with Human Endostatin Protein Accucyte® EIA kit. It is determined that the effective blood drug concentration of the modified endostatin is increased more than 20 times (FIG. 7), and the in vivo half-life is 18 h for $PEG_{20}$-ENDO and 97 h for $PEG_{40}$-ENDO, while it is 8 h for Endostar. The AUC is improved at least 10 times for $PEG_{20}$-ENDO and at least 100 times for $PEG_{40}$-ENDO, compared to that of Endostar.

($AUC_{0-\infty}$ of Endostar=1065.46 µg/L*h; $C_{0-\infty}$ of $PEG_{20}$-ENDOAU=1133103.46 µg/L*h; $AUC_{0-\infty}$ of $PEG_{40}$-ENDO=19759375.66 µg/L*h)

Embodiment 4 Determination of Bioactivity of Polyethylene Glycol-Modified Endostar 1. The bovine aortic endotheliocytes were cultured in a RPMI-1640 medium containing 10% fetal bovine serum, placed into an incubator at 37° C., 5% $CO_2$ and cells in log growth phase were selected for experiment.

2. The cell concentrations (10000/ml) were adjusted and divided into 10 groups to seed on a 96-well plate with 5 duplicate wells set for each group, placed into an incubator at 37° C., 5% $CO_2$ for 24 h, and Endostar, $PEG_{20}$-ENDO and $PEG_{40}$-FNDO were added respectively at the final concentration of 100 µg/ml, 25 µg/ml, 6.25 µg/ml, 1.56 µg/ml, 0.39 µg/ml after cell adherence. For the control group, 1640 medium containing 2% FCS and 1640 medium containing 2% FCS+bFGF were added, and the wells were sealed with 1640 medium containing 2% FCS in the last 4 weeks.

3. OD value of each well was measured by MTT method. Inhibition rate was calculated according to the OD value, and the calculation formula is Inhibition Rate (IR)=(mean OD value of the control group−mean OD value of the experimental group)/mean OD value of the control group.

Figure 8:
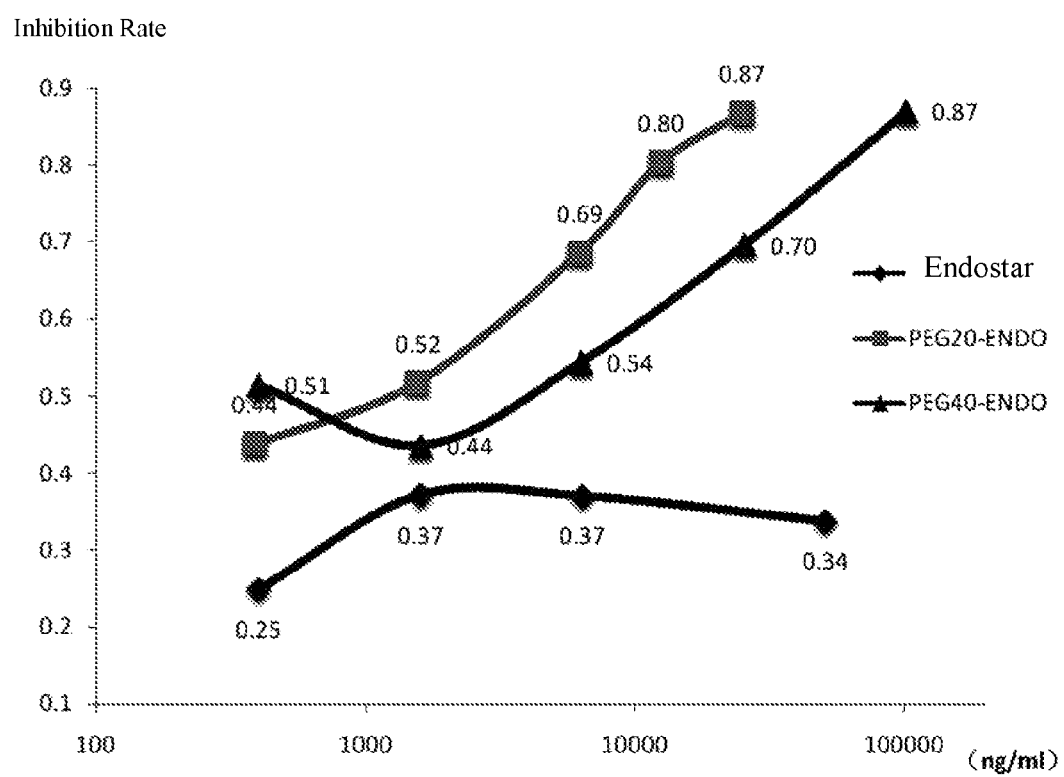
FIG. 8 shows the activity of Endostar before and after modification in inhibiting endotheliocyte proliferation.

4. The activity of inhibiting endotheliocyte proliferation of $PEG_{20}$-ENDO and $PEG_{40}$-ENDO is significantly increased, in which the activity of $PEG_{20}$-ENDO is increased more (FIG. 8).

What is claimed is:

1. A modified recombinant endostatin, having a structure of:

$CH_3O-(CH_2CH_2O)_m-CH_2CH_2CH_2-N^{\alpha}H$-Endostar, wherein a weight average molecular weight of $CH_3O-(CH_2CH_2O)_m-CH_2CH_2CH_2-$ is 40 kD; and wherein an amino acid sequence of said Endostar is selected from the group consisting of SEQ ID NO: 1 and SEQ ID NO: 2, wherein the in vivo half-life of the modified recombinant endostatin is 97 h.

* * * * *

SEQUENCE LISTING

```
<160> NUMBER OF SEQ ID NOS: 2

<210> SEQ ID NO 1
<211> LENGTH: 192
<212> TYPE: PRT
<213> ORGANISM: Artificial sequence
<220> FEATURE:
<223> OTHER INFORMATION: Recombinant human endostatin expressed by E.
      coli

<400> SEQUENCE: 1

Met Gly Gly Ser His His His His His His Ser His Arg Asp Phe
1               5                   10                  15

Gln Pro Val Leu His Leu Val Ala Leu Asn Ser Pro Leu Ser Gly
                20                  25                  30

Gly Met Arg Gly Ile Arg Gly Ala Asp Phe Gln Cys Phe Gln Gln
                35                  40                  45

Ala Arg Ala Val Gly Leu Ala Gly Thr Phe Arg Ala Phe Leu Ser
                50                  55                  60

Ser Arg Leu Gln Asp Leu Tyr Ser Ile Val Arg Arg Ala Asp Arg
                65                  70                  75
```

```
Ala Ala Val Pro Ile Val Asn Leu Lys Asp Glu Leu Leu Phe Pro
                80                  85                  90

Ser Trp Glu Ala Leu Phe Ser Gly Ser Glu Gly Pro Leu Lys Pro
                95                 100                 105

Gly Ala Arg Ile Phe Ser Phe Asp Gly Lys Asp Val Leu Arg His
               110                 115                 120

Pro Thr Trp Pro Gln Lys Ser Val Trp His Gly Ser Asp Pro Asn
               125                 130                 135

Gly Arg Arg Leu Thr Glu Ser Tyr Cys Glu Thr Trp Arg Thr Glu
               140                 145                 150

Ala Pro Ser Ala Thr Gly Gln Ala Ser Ser Leu Leu Gly Gly Arg
               155                 160                 165

Leu Leu Gly Gln Ser Ala Ala Ser Cys His His Ala Tyr Ile Val
               170                 175                 180

Leu Cys Ile Glu Asn Ser Phe Met Thr Ala Ser Lys
               185                 190

<210> SEQ ID NO 2
<211> LENGTH: 191
<212> TYPE: PRT
<213> ORGANISM: Artificial sequence
<220> FEATURE:
<223> OTHER INFORMATION: Recombinant human endostatin expressed by E.
      coli

<400> SEQUENCE: 2

Gly Gly Ser His His His His His Ser His Arg Asp Phe Gln
  1               5                  10                  15

Pro Val Leu His Leu Val Ala Leu Asn Ser Pro Leu Ser Gly Gly
                20                  25                  30

Met Arg Gly Ile Arg Gly Ala Asp Phe Gln Cys Phe Gln Gln Ala
                35                  40                  45

Arg Ala Val Gly Leu Ala Gly Thr Phe Arg Ala Phe Leu Ser Ser
                50                  55                  60

Arg Leu Gln Asp Leu Tyr Ser Ile Val Arg Arg Ala Asp Arg Ala
                65                  70                  75

Ala Val Pro Ile Val Asn Leu Lys Asp Glu Leu Leu Phe Pro Ser
                80                  85                  90

Trp Glu Ala Leu Phe Ser Gly Ser Glu Gly Pro Leu Lys Pro Gly
                95                 100                 105

Ala Arg Ile Phe Ser Phe Asp Gly Lys Asp Val Leu Arg His Pro
               110                 115                 120

Thr Trp Pro Gln Lys Ser Val Trp His Gly Ser Asp Pro Asn Gly
               125                 130                 135

Arg Arg Leu Thr Glu Ser Tyr Cys Glu Thr Trp Arg Thr Glu Ala
               140                 145                 150

Pro Ser Ala Thr Gly Gln Ala Ser Ser Leu Leu Gly Gly Arg Leu
               155                 160                 165

Leu Gly Gln Ser Ala Ala Ser Cys His His Ala Tyr Ile Val Leu
               170                 175                 180

Cys Ile Glu Asn Ser Phe Met Thr Ala Ser Lys
               185                 190
```